United States Patent [19]

Yang

[11] 4,168,376

[45] Sep. 18, 1979

[54] PROCESS FOR CRYSTALLINE SODIUM CEFAMANDOLE

[75] Inventor: Kuo S. Yang, Greenwood, Ind.

[73] Assignee: Eli Lilly and Company, Indianapolis, Ind.

[21] Appl. No.: 912,613

[22] Filed: Jun. 5, 1978

[51] Int. Cl.$^2$ .......................................... C07D 501/36
[52] U.S. Cl. ...................................... 544/26; 424/246
[58] Field of Search ......................................... 544/26

[56] References Cited

U.S. PATENT DOCUMENTS

| 3,641,021 | 2/1972 | Ryan | 544/26 |
|---|---|---|---|
| 4,006,138 | 2/1977 | Yang | 544/26 |
| 4,054,738 | 10/1977 | Yang | 544/26 |

OTHER PUBLICATIONS

Indelicato, et al., Jour. Pharm. Sciences, G5 No. 8 (1976) pp. 1175–1178.

*Primary Examiner*—Nicholas S. Rizzo
*Attorney, Agent, or Firm*—William B. Scanlon; Arthur R. Whale

[57] ABSTRACT

A suspension of substantially pure sodium 7-(D-α-formyloxy-α-phenylacetamido)-3-(1-methyl-1H-tetrazol-5-ylthiomethyl)-3-cephem-4-carboxylate in methyl alcohol containing about 2% water on treatment with a methyl alcohol solution of sodium hydroxide is converted to a crystalline suspension of sodium 7-(D-α-hydroxy-α-phenylacetamido)-3-(1-methyl-1H-tetrazol-5-ylthiomethyl)-3-cephem-4-carboxylate in yields of about 65 to 70%.

1 Claim, No Drawings

PROCESS FOR CRYSTALLINE SODIUM CEFAMANDOLE

BACKGROUND OF THE INVENTION

Description of the Prior Art

Ryan, U.S. Pat. No. 3,641,021, describes the broad spectrum antibiotic cefamandole and its salts such as the sodium salt. Cefamandole has the chemical name 7-(D-α-hydroxy-α-phenylacetamido)-3-(1-methyl-1H-tetrazol-5-ylthiomethyl)-3-cephem-4-carboxylic acid or, alternatively, 7-D-mandelamido-3-(1-methyl-1H-tetrazol-5-ylthiomethyl)-3-cephem-4-carboxylic acid. Ryan also describes the formyl ester of cefamandole, 7-(D-α-formyloxy-α-phenylacetamido)-3-(1methyl-1H-tetrazol-5-ylthiomethyl)-3-cephem-4-carboxylic acid. This formate ester formed with the α-hydroxy group of the 7-position side chain is described by Ryan as an intermediate in the synthesis of cefamandole.

Greene and Indelicato, U.S. Pat. No. 3,928,592, disclose the sodium salt of the formate ester of cefamandole, known as O-formylcefamandole, as a useful prodrug of cefamandole and describe pharmaceutical formulations useful for parenteral administration. O-Formylcefamandole is described as a stable, crystalline compound which, in contrast with cefamandole itself, is readily purified.

Yang, U.S. Pat. No. 4,006,138, describes the crystalline anhydrate form of O-formylcefamandole sodium designated as the gamma crystalline form, which is stable under conditions of relatively high atmospheric moisture. Yang, U.S. Pat. No. 4,054,738, also describes the new anhydrate, monohydrate and methanolate crystalline forms of sodium cefamandole and their interconversion.

J. M. Indelicato, et al., Journal of the Pharmaceutical Sciences, 65, [8], 1175–1178, (1976) reports studies of the hydrolysis rate of sodium O-formylcefamandole.

SUMMARY OF THE INVENTION

This invention relates to a process for preparing the crystalline methanolate form of sodium cefamandole. In particular, it relates to a process for preparing the crystalline methanolate form of sodium cefamandole which comprises the treatment of a methanolic suspension of sodium O-formylcefamandole with a concentrated methanolic solution of sodium hydroxide to provide a suspension of crystalline sodium cefamandole methanolate.

DETAILED DESCRIPTION

According to the process of this invention, a suspension of sodium O-formylcefamandole in methyl alcohol is mixed with a concentrated solution of sodium hydroxide in methyl alcohol to form a suspension of the crystalline methanolate form of sodium cefamandole. The process is illustrated by the following reaction scheme.

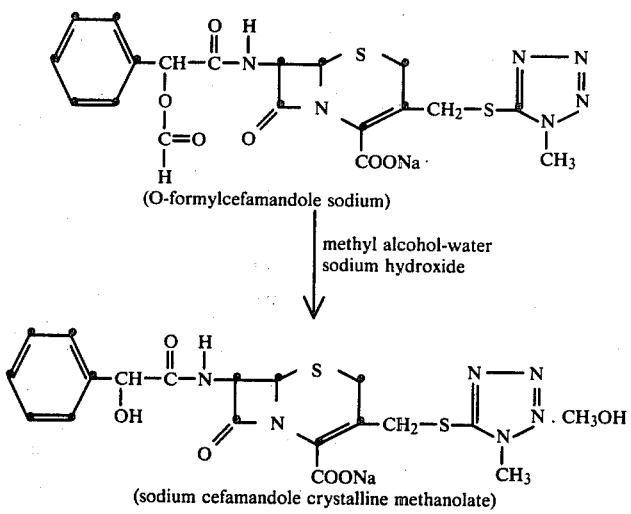

As shown above, the process involves the hydrolysis of the formate ester of O-formylcefamandole sodium under basic conditions to cefamandole sodium. The sodium cefamandole is obtained in crystalline form as the methanolate. This crystalline form is described in U.S. Pat. No. 4,054,738 issued Oct. 18, 1977.

According to the process of this invention, substantially pure crystalline sodium O-formylcefamandole is suspended in methyl alcohol containing between about 1.5 percent and about 3 percent water by volume and the suspension is mixed with a concentrated solution of sodium hydroxide in methyl alcohol. The suspension is agitated vigorously by rapid stirring or shaking during the addition of the sodium hydroxide solution. The crystalline sodium cefamandole methanolate forms in the suspension and after addition of the base is complete, the crystals are harvested without delay to prevent decomposition in the basic mother liquor.

The suspension of sodium O-formylcefamandole in methyl alcohol used in the process contains about one gram of sodium O-formylcefamandole in a volume of methyl alcohol of between about 2.5 ml. and about 3.5 ml. As noted above, between about 1.5 percent and about 3 percent by volume of water is included in the suspension. The amount of water is critical since it is essential in the process that the sodium cefamandole methanolate produced be substantially insoluble in the basic reaction mixture. Excess water in the suspension will promote solubility of the hydrolysis product which in the basic medium will undergo decomposition with an accompanying decrease in yield.

The concentrated solution of sodium hydroxide in methyl alcohol is added slowly to the suspension of sodium O-formylcefamandole with vigorous agitation.

Sufficient concentrated solution of sodium hydroxide is added to adjust the pH of the suspension to between about 8 and about 10. The pH of the suspension was measured indirectly by removing an aliquot and determining the pH of the water diluted aliquot with a pH meter. The desired basicity of the suspension is achieved by adding about 1 ml. of a concentrated methanolic sodium hydroxide solution per gram of sodium O-formylcefamandole in suspension. A concentrated methanol solution of sodium hydroxide contains about 12 mg./ml.

The amount of sodium hydroxide added is critical in the process since an excess will cause decomposition associated with $\beta$-lactam scission as well as with other routes of decomposition. Too low a concentration of sodium hydroxide will not achieve the basicity at which the hydrolysis of the formate ester proceeds at a practical rate.

The process is carried out at a temperature between about 20° C. and about 30° C. and conveniently at about 25° C.

As mentioned above, the sodium O-formylcefamandole used in the process is substantially pure. Substantially pure refers to a purity above about 95%. The O-formylcefamandole sodium salt is sparingly soluble in methyl alcohol containing the low percentage by volume of water employed in the present process. Although the solubility of various crystalline forms of sodium O-formylcefamandole for example, the $\alpha$, $\beta$ and $\gamma$ forms described by U.S. Pat. No. 4,006,138 can differ in their solubilities, they are all sparingly soluble in methyl alcohol. It appears, however, that the hydrolysis of the formate ester occurs with the small amount of ester which is in solution rather than at the surface of the suspended crystals. The latter site of hydrolysis is, however, not ruled out.

When the process of this invention is carried out, the crystalline suspension of sodium O-formylcefamandole is converted to a crystalline suspension of sodium cefamandole methanolate without a complete solution occurring. One observes the transformation of the crystalline suspension without any noticeable change in the amount of suspended crystals. Following the addition of the concentrated methyl alcohol solution of sodium hydroxide, the suspension is vigorously stirred for about 15 to 30 minutes during which time the hydrolysis is completed and crystals of sodium cefamandole methanolate have formed. The crystals are harvested promptly to avoid decomposition in the basic medium. The crystals can be harvested by conventional methods such as filtration, centrifugation, etc. After separation from the mother liquor the crystals are washed with methanol and ether and are dried. Yields of sodium cefamandole methanolate of between about 65 and about 70% are generally obtained in the process.

The sodium cefamandole methanolate obtained in the process can be converted to the anhydrate crystalline form for pharmaceutical use as described by U.S. Pat. No. 4,054,738.

The following example further describes the process of this invention.

EXAMPLE

To a suspension of 10 g. of pure sodium 7-(D-$\alpha$-formyloxy-$\alpha$-phenylacetamido)-3-(1-methyl-1H-tetrazol-5-ylthiomethyl)-3-cephem-4-carboxylate in 20 ml. of 98% methyl alcohol was slowly added at room temperature a solution of 120 mg. of sodium hydroxide in 10 ml. of methyl alcohol. The suspension was stirred vigorously throughout the addition and after about 15 minutes with continued stirring, the crystals of sodium 7-(D-$\alpha$-hydroxy-$\alpha$-phenylacetamido)-3-(1-methyl-1H-tetrazol-5-ylthiomethyl)-3-cephem-4-carboxylate methanolate which formed from the suspension were filtered. The crystalline precipitate was washed with methanol and with ether and was air dried. The yield of product was 65% of theoretical. The X-ray powder diffraction pattern of the crystalline methanolate obtained with nickel filtered copper radiation of 1.5405 A is shown below.

| Spacing d | Relative Intensity $I/I_1$ |
|---|---|
| 15.22 | .06 |
| 14.24 | 1.00 |
| 12.99 | .25 |
| 8.75 | .18 |
| 7.92 | .19 |
| 7.65 | .45 |
| 7.16 | .46 |
| 6.93 | .25 |
| 6.62 | .18 |
| 5.48 | .15 |
| 5.30 | .07 |
| 5.11 | .26 |
| 4.98 | .47 |
| 4.79 | .40 |
| 4.64 | .19 |
| 4.22 | .08 |
| 4.15 | .07 |
| 3.76 | .11 |
| 3.89 | .28 |
| 3.70 | .18 |
| 3.58 | .19 |
| 3.49 | .22 |
| 3.35 | .13 |
| 3.12 | .09 |
| 2.93 | .06 |
| 2.89 | .17 |
| 2.79 | .10 |
| 2.76 | .08 |
| 2.66 | .09 |
| 2.56 | .07 |

I claim:

1. A process for preparing the methanolate crystalline form of sodium cefamandole which comprises the steps (a) mixing at a temperature between about 20° C. and about 30° C. a suspension of sodium O-formylcefamandole in methyl alcohol having a ratio of about one gram of sodium O-formylcefamandole for between about 2.5 ml. and about 3.5 ml. of methyl alcohol, said suspension containing between about 1.5 percent and about 3 percent by volume of water, with a concentrated solution of sodium hydroxide in methyl alcohol in an amount corresponding to about 1 ml. of said concentrated solution per gram of sodium O-formylcefamandole in said suspension, and (b) separating the crystalline sodium cefamandole methanolate from the suspension.

* * * * *